United States Patent
Czech et al.

(10) Patent No.: US 6,207,782 B1
(45) Date of Patent: Mar. 27, 2001

(54) HYDROPHILIC SILOXANE LATEX EMULSIONS

(75) Inventors: Anna Czech, Cortlandt Manor; Kalman Koczo, Suffern, both of NY (US)

(73) Assignee: Cromption Corporation, Middlebury, CT (US)

(*) Notice: Subject to any disclaimer, the term of this patent is extended or adjusted under 35 U.S.C. 154(b) by 0 days.

(21) Appl. No.: 09/151,468

(22) Filed: Sep. 11, 1998

Related U.S. Application Data

(63) Continuation-in-part of application No. 09/086,391, filed on May 28, 1998, now abandoned.

(51) Int. Cl.⁷ ............................ C08G 77/04; C08L 83/04
(52) U.S. Cl. .............................. 528/26; 528/52; 526/279; 524/837; 524/845; 524/765; 524/731; 424/70.12; 424/401; 424/59; 424/64
(58) Field of Search ..................... 528/26, 32; 526/279; 524/837, 845, 765, 732; 424/70.12, 401, 59, 64

(56) References Cited

U.S. PATENT DOCUMENTS

| 4,584,337 | * | 4/1986 | Lee et al. ............................ 524/500 |
| 4,851,216 | | 7/1989 | Lee . |
| 4,990,360 | | 2/1991 | Gornowcz et al. . |
| 5,084,489 | | 1/1992 | Liles ........................................ 522/84 |
| 5,171,638 | | 12/1992 | Ozaki et al. ........................... 428/447 |
| 5,567,428 | * | 10/1996 | Hughes .................................. 424/401 |
| 5,612,433 | | 3/1997 | Ono et al. ............................ 526/279 |
| 5,635,546 | | 6/1997 | Rich et al. ............................ 523/176 |
| 5,733,971 | | 3/1998 | Feldmann-Krane et al. . |

\* cited by examiner

Primary Examiner—Robert Dawson
Assistant Examiner—Jeffrey B. Robertson
(74) Attorney, Agent, or Firm—Scully, Scott, Murphy & Presser

(57) ABSTRACT

Emulsions and dispersions of polymers formed from acrylated hydrophilic polysiloxanes and their copolymers with acrylate/methacrylate comonomers are taught herein wherein the polymer is formed in a solvent via radically catalyzed polymerization. Such a polymer has utility in personal care applications, as well as textile finishes and coating formulations.

20 Claims, No Drawings

HYDROPHILIC SILOXANE LATEX EMULSIONS

This application is a continuation-in-part of U.S. patent application Ser. No. 09/086,391, filed May 28, 1998 now abandoned.

BACKGROUND OF THE INVENTION

Acrylated polysiloxanes copolymerized with organic acrylates and emulsions thereof are known wherein the siloxane and acrylate have been applied to a substrate and are polymerized directly onto a surface. For example, U.S. Pat. No. 5,635,546 teaches a curable composition, having utility for threadlocking engageable members of a threaded mechanical fasteners. An emulsion of the reactive silicone acrylate and optional other polymerizable acrylate monomer is applied onto the engagement surface and polymerizing in situ to lock parts in place.

Another example, U.S. Pat. No. 5,171,638 teaches organopolysiloxane/acrylate ester copolymer emulsion compositions which offer release, antisoiling and water repellency for paints and textile. Similarly U.S. Pat. No. 5,612,433 describes monofunctional dimethysiloxane acrylates copolymerized with acrylate/methacrylate ester to produce water repellent films on fibers. Additional examples of the emulsified acrylate/methacrylate copolymers with hydrophobic organopolysiloxane, primarily intended for use in paints, is provided in U.S. Pat. No. 5,084,489.

SUMMARY OF THE INVENTION

Emulsions of polymers derived from hydrophilic acrylated siloxanes, offer such important properties like hydrophilicity and rewettability while maintaining other "silicone" characteristics, such as improved aesthetics and tactile properties. The use of these emulsions and copolymer formulations of these emulsions are also taught herein.

DETAILED DESCRIPTION OF THE INVENTION

The present invention describes radically polymerized acrylates/methacrylates of polyether modified polysiloxanes and their copolymers with organic acrylates, as well as emulsions including these polymers. The siloxanes have siloxane backbones with pendant polyether functionalities which polyethers are encapped with an acrylate or methacrylate functionality. The backbone may be linear, branched or cyclic. These acrylated siloxanes then are polymerized in a solvent to form an emulsion of the latex.

The acrylated siloxanes can be represented by Formula I

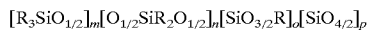

wherein R is selected from the $R^1$ and P, wherein each $R^1$ can be the same or different and each is a monovalent hydrocarbon group; each P is $R^3[O(C_bH_{2b}O)_z COCR^4=CH_2]_g$ wherein, $R^3$ is a poly valent organic moiety, which may be hydroxy substituted alkylene, g is the valency of $R^3$ minus 1, $R^4$ is hydrogen or methyl; b=2 to 4, preferably 2 to 3; z=1 to 1000, preferably 3 to 30; and m+n+p+o=1 to 100, preferably 2 to 20, at least one R is P; n=1 to 100; when O is not zero n/o<10:1; when p is not zero n/p<10:1; and m=0 to 10.

Preferably the acrylated siloxane is of the formula (II)

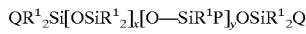

wherein x, and y can be 0 or an integer, preferably each x and y are from 0 to 100, most preferably 0 to 25; Q can be $R^1$ or P, with the proviso that the average acrylate functionality is >1 unsaturated groups per molecule. In the preferred embodiment y=0 and Q=P.

Preferably R is a $C_1$–$C_4$ alkyl, an aryl or alkaryl. Specifically preferred R are methyl, ethyl, phenyl and ethyl phenyl. R may include heteroatom substituents preferably, which are nonreactive with acrylates.

P may be branched with several polyether branches originating from the alkyl bridge to the silicon atom. For example, P may be an alkoxylated trimethylol propane monoallyl ether which has been hydrosilated onto the siloxane backbone and esterified. Other polyvalent precursors for P, which may be hydrosilated, alkoxylated and esterified are glycerol monoallyl ether, pentaerythritol allyl ether and trisopropanol amine allyl ether. In a preferred embodiment, g=1 and $R^3$ is a linear $C_2$–$C_5$ alkylene, most preferably $C_2$–$C_3$.

Not all polyethers in P need be the same as each other. Preferable P structures are ones with ethylene oxide (b=2) contents of greater than 80% by weight of the alkylene oxide ($C_bH_{2b}O$) content, most preferably all of the alkylene oxide chain is ethylene oxide.

Said acrylates of Formula I are derived from the polyether polysiloxane copolymers wherein the polyethers are attached to the siloxane backbone through a non-hydrolyzable Si—C bond. Moreover, the polyethers should be uncapped so that the hydroxyl group may be (trans) esterified with the acrylate. Said polyether polysiloxanes are commercially available.

The esterification is catalyzed with a Bronstead acid if the acid is the starting acrylate. If an ester is used an acid or base can be used to catalyze the transesterification.

The acrylated silicone copolymers are polymerized to form polymers (latexes), or if desired, copolymers of Formula I with other comonomers (e.g., other esters). Said polymerization may be conducted in various solvents, catalysts and temperatures as are known in the art for polymerizing acrylates. Said polymerization should not be conducted on a surface to form a film. Rather, polymerization in a solvent allows for production of a crosslinked latex gel which has broader utility than film forming. The emulsion should contain less than or equal to 90 wt %, preferably less than 50 wt %, of the polymer in solvent. Suitable solvents include polar solvents, e.g., water and alcohol, and non-polar solvents, such as many hydrocarbons or low molecular weight cyclic or linear polydimethylsiloxanes. Preferably polydimethylsiloxanes should have a viscosity of less than 100 cSt (25° C.).

Any organic acrylate or methacrylate can be employed in forming the copolymers with Formula I. Thus, for example, acrylic acid and methacrylic acid or their derivatives such as esters, nitrites and amides can be employed. The esters are preferred compounds. Specific examples of the acrylates that can be utilized are methyl acrylate, ethyl acrylate, butyl acrylate, amyl acrylate, 2-ethylhexyl acrylate, cyclohexyl acrylate, vinyl acrylate, allyl acrylate, hydroxyethyl acrylate, perfluoroethyl acrylate, isobornyl acrylate, phenoxyethyl acrylate, tetraethylene glycol diacrylate, tripropylene glycol diacrylate, trimethylolpropane triacrylate. A single acrylate or various combinations of acrylates can be employed in making the copolymers.

Copolymers of the acrylates/methacrylates of the polyether modified polysiloxanes, with the organic acrylates may consist of 1 to 99% by weight of the polysiloxanes, preferably 20–90% and most preferably 50–80% of the polysiloxane.

It is also an objective of the present invention to produce emulsions, comprising the polymerized acrylates/ methacrylates polyether polysiloxanes copolymers and/or their copolymers with organic acrylates (i.e., latexes), which upon evaporation of water form films with good tactile properties and good integrity. These emulsions may in fact be dispersions of the latex.

One particular method to prepare emulsions is:
1. Dispersing an acrylate/methacrylate of polyether polysiloxane copolymers, as defined by Formula I, with or without a separate organic acrylate, using at 5–50% by weight of the siloxane emulsifiers selected from nonionic surfactants (such as alkylaryl-polyoxyethylene adducts and alkyl ethoxylates) or anionic surfactants (such as, carboxylates, sulfates, sulfonates, alkylaryl sulfonates and alkyl phosphates), to form a stable emulsion containing 10–50% of the dispersed siloxane phase, which can be further stabilized by addition of common thickeners, such as xanthan or guar gum, gellatin and cellulose derivatives.
2. Adding a free-radical catalyst, selected from the group of water soluble or oil soluble peroxides, such as hydrogen peroxide, ammonium persulfate, potassium persulfate, various organic peroxy catalysts, such as dialkyl peroxides, e.g., diisopropyl peroxide, dilauryl peroxide, di-t-butyl peroxide, dicumyl peroxide, alkyl hydrogen peroxides such as t-butyl hydrogen peroxide, t-amyl hydrogen peroxide, cumyl hydrogen peroxide, diacyl peroxides, for instance acetyl peroxide, lauroyl peroxide, benzoyl peroxide, peroxy ester such as ethyl peroxybenzoate, the azo compounds such as 2-azobis (isobutyronitrile), to the emulsion.
3. Heating the emulsion to or above the temperature necessary for initiating the radical reaction, typically 40 to 100° C., depending on the catalyst, for 1–10 hours or until the unsaturated groups are consumed.

Alternatively, a water in oil emulsions, particularly water in polysiloxane emulsions, are prepared by combining water, anionic surfactant (e.g., sodium dodecyl sulfate) and free radical catalyst, in the aqueous phase and adding the acrylated/methacrylated polyether polysiloxane copolymer, followed by the polysiloxane and silicone surfactant to the agitated aqueous phase. The HLB of the anionic surfactant should be relatively high, i.e., above about 15, and the HLB of the silicone surfactant should be between about 4 and 9. Examples of the silicone surfactant are SILWET L-7622 and SILWET FZ 2108 (available from OSi Specialties, Inc., a subsidiary of Witco Corporation). The preformed emulsion is heated to at least about 80–90° C. for about 2 to 4 hours. The copolymer should be present at 20–60 wt % of the emulsion and the internal aqueous phase should be present at 5–25 wt % of the emulsion. The polysiloxane should be present at 25–75 wt % of the emulsion. The amount of surfactants will be determined for each case as necessary.

Use

The emulsion may be translucent or milky, depending on the acrylate/methacrylate used. The emulsions are stable with no separation at up to about 90° C. The viscosity of the emulsion can be from 0.01 to 10,000 cps (25° C.). The dry oil phase (i.e., after the solvent has evaporated from the emulsion) can form smooth and soft films to stiff and brittle films, depending on the starting material and ratio of silicone to acrylate. Generally, the higher the silicone content, the softer the film.

The emulsions of the present invention can be used as ingredients of personal care formulations, including skin care, nail care, and hair care formulations, such as lipsticks, mascaras, nail polishes, foundations, lotions, creams, sunscreens, shampoos and conditioners, to improve their wear, tactile properties, and ease of application. They also can be used in textile and fiber treatments to impart smooth, soft feel and wettability to both natural and synthetic substrates including natural fibers such as hair, cotton, silk, flax and wool; synthetic fibers such as polyester, polyamide, polyacrylonitrile, polyethylene, polypropylene and polyurethane; and inorganic fibers such as glass or carbon fibers. The fabric substrate which can be treated with the copolymers of the present invention is exemplified by the fabric produced from the above-mentioned fibrous materials or blends thereof. These emulsions can be applied onto the substrate such as by spraying, dipping or kiss roll application or other application method typically employed in hair or textile treatment.

In general the emulsion is applied on skin, hair, fiber, textile or other substrate such that up to 5%, preferable 0.01 to 2.5% of the polymer by weight of the dry substrate remains on the substrate. Optionally other additives, commonly used to treat hair or textile substrates can be employed along with the copolymers of the present invention, including but not limited to additional surfactants, curing resins, preservatives, dyes, colorants, formularies.

Finally, the emulsions of the present invention can be incorporated into waterborne coating formulations for metals, plastic, wood and paper, such as varnishes, latex paints and roofing compositions.

Some sample formulations incorporating the latexes of the present invention are:

SHAMPOO—comprising:
  a) an anionic surfactant, a zwitterionic surfactant, an amphotheric surfactant or mixtures of;
  b) long chain acyl derivative or long chain amine oxide suspending agents selected from alkanolamides, ethylene glycol long chain esters, glyceryl long chain esters and mixtures thereof; and
  c) water.

LIPSTICK—comprising:
  a) waxes such as carnauba wax, beeswax, ozokerite, ceresin, candelilla wax and parafin wax;
  b) oils selected from castor oil, ester oils, mineral oils and vegetable oils;
  c) pigments; and
  d) other functional additives such as wetting agent, antioxidants.

FACIAL MAKEUP—oil in water, water in oil or oil free systems comprising:
  a) pigments;
  b) dispersion stabilizers selected from emulsifiers such as glyceryl monostearate or polysorbate 60, thickeners such as veegum, cellulose derivatives, xanthan gum;
  c) oils selected from mineral oils, vegetable oils, ester oils; and
  d) other functional ingredients, such as pigment dispersants, antioxidants and uv absorbers

EXAMPLES

Example 1

Preparation of the Hydrophilic Silicone Latexes

An acrylate was added slowly to the water/surfactant mixture, followed by the catalyst. The charges are summarized in Table 1. The emulsion was heated with agitation to 75–80° C. for 1 to 2 hour. After cooling to room temperature, solid sodium bicarbonate was added to adjust pH of the emulsion to neutral.

Evaluation of Film Forming Properties

Five ml samples of Emulsions I–XI were placed on the glass panel and dried at room temperature. Results are provided in Table 2.

TABLE 1

Charges for the Preparation of the Hydrophilic Silicone Latexes

| Emulsion ID | Acrylate | Acrylate Charge | Water Charge | Sodium Lauryl Sulfate Charge | Catalyst | Catalyst Charge |
|---|---|---|---|---|---|---|
| I | Polysiloxane A*) | 40.0 g | 155.8 g | 4.0 g | potassium persulfate | 0.2 g |
| II | Polysiloxane B**) | 40.0 g | 155.8 g | 4.0 g | potassium persulfate | 0.2 g |
| III | Polysiloxane A 2-Ethylhexyl acrylate | 20.0 g 20.0 g | 155.8 g | 4.0 g | potassium persulfate | 0.2 g |
| IV | Polysiloxane A 2-Ethylhexyl acrylate | 30.0 g 10.0 g | 155.8 g | 4.0 g | potassium persulfate | 0.2 g |
| V | Polysiloxane A 2-Phenoxyethyl acrylate | 20.0 g 20.0 g | 155.8 g | 4.0 g | potassium persulfate | 0.2 g |
| VI | Polysiloxane B 2-Phenoxyethyl acrylate | 20.0 g 20.0 g | 155.8 g | 4.0 g | potassium persulfate | 0.2 g |
| VII | Polysiloxane A Isobornyl acrylate | 20.0 g 20.0 g | 155.8 g | 4.0 g | potassium persulfate | 0.2 g |
| VIII | Polysiloxane A Tripropylene glycol diacrylate | 20.0 g 20.0 g | 155.8 g | 4.0 g | potassium persulfate | 0.2 g |
| IX | Polyxiloxane A | 80.0 g | 111.6 | 8.0 g | potassium persulfate | 0.4 g |
| X | Polysiloxane A | 40.0 g | 155.8 g | 4.0 g | ammonium persulfate | 0.2 g |
| XI | Tripropylene glycol dicacrylate | 40.0 g | 155.8 g | 4.0 g | potassium persulfate | 0.2 g |

*)Polysiloxane A:
$CH_2=CH—CO(OC_2H_4)_8OC_3H_6Si(CH_3)_2[-OSi(CH_3)_2]_{15}OSi(CH_3)_2C_3H_6O(C_2H_4O)_8COCH=CH_2$
**)Polyxilosane B:
$CH_2=CH—CO(OC_2H_4)_8OC_3H_6Si(CH_3)_2[—OSi(CH_3)_2]_{10}OSi(CH_3)_2C_3H_6O(C_2H_4O)_8COCH=CH_2$

TABLE 2

Film Forming Properties of Silicone Latex Emulsions I-XI

| Emulsion ID | Film Properties |
|---|---|
| I | uniform, smooth, soft, dry |
| II | uniform, smooth, soft, dry |
| III | uniform, sticky |
| IV | uniform, slightly sticky, soft |
| V | brittle |
| VI | uniform, soft |
| VII | brittle |
| VIII | uniform, smooth, soft, dry |
| IX | uniform, smooth, soft, dry |
| X | uniform, smooth, soft, dry |
| XI | brittle solid |

Most of the Silicone Latex Emulsions formed uniform, smooth, soft and dry films, while the organic acrylate (Emulsion XI) produced brittle solids.

Emulsion XII

Polysiloxane A (50 g) was combined with 20 g of and aqueous 2% solution of ammonium persulfate and 0.5 g of sodium dodecyl sulfate. This mixture was added slowly, with mixing, to a blend of 50 g of decamethyl cyclopentasiloxane and 5 g of SILWET FZ-2108 silicone surfactant (OSi Specialties). The resulting emulsion was stirred and heated to 80–85° C. for 2 hours resulting in a stable water in polysiloxane emulsion.

Example 2

Application of the Hydrophilic Silicone Latexes in Lipstick Formulations

Five weight percent of the silicone latex emulsions I, IV, VI, VIII and XI were combined with the ingredients of the Control Lipstick Formulation. The ease of application, gloss and non-transfer properties were evaluated. Gloss was evaluated visually after applying lipsticks to skin; non-transfer was tested by blotting white facial tissue and visually evaluating coloration on the tissue. Results are summarized in Table 3.

Model Formulation: Control Lipstick

| Ingredients: | parts |
|---|---|
| Carnuba Wax | 13.70 |
| Syncrowax BB4 (Croda) | 8.50 |
| Castor Oil | 32.8 |
| Isopropyl Myristate | 30.0 |
| Cloisonne Red Pigment (Mica, TiO$_2$, Carmine-Mearl Corp.) | 15.0 |

Mixing Procedure: Combine ingredients, mix and heat to 80° C. or until melted and uniform. Pour into the mold.

TABLE 3

Evaluation of Lipstick Formulations.

| Formulation | Comments |
|---|---|
| Control Lipstick Formulation | easy to apply, moderate gloss, significant blotting |
| Control Lipstick Formulation + Emulsion XI | draggy, dull, less transfer than control |
| Control Lipstick Formulation + Emulsion VIII | easy to apply, high gloss, less transfer than control |
| Control Lipstick Formulation + Emulsion VI | easy to apply, high gloss, less transfer than control |
| Control Lipstick Formulation + Emulsion IV | easy to apply, high gloss, less transfer than control |
| Control Lipstick Formulation + Emulsion I | easy to apply, high gloss, less transfer than control |

All hydrophilic silicone latex emulsions I, IV, VI and VIII improved non-transfer properties and gloss of the lipsticks; organic acrylate emulsion (XI) also reduced the transfer but at the same time negatively affected the feel and gloss.

Example 3
Application of the Hydrophilic Silicone Latexes in Foundations

Five weight percent of the silicone latex emulsions I, IV, VIII and XI were post added to the pre-formed Control Foundation Cream. The ease of application, spreadability and after-feel were evaluated. Results are summarized in Table 4.

Model Formulation: Control Foundation Cream

|  | parts |
|---|---|
| Phase I | |
| Stearic Acid | 12.0 |
| Isopropyl Myristate | 1.0 |
| Glyceryl Monostearate | 2.0 |
| Polysorbate 60 NF | 1.0 |
| Sorbitan Monostearate | 2.0 |
| Propylene Glycol | 12.0 |
| Phase II | |
| pigments* | 3.0 |
| Water | qs |
| PIGMENTS COMPOSITION: | |
| Microna Matte White | 79.6parts |
| Red | 9.6 |
| Yellow | 9.8 |
| Black | 1.0 |

Procedure: Heat Phase I to 65° C., add phase II with mixing. Cool to 35° C., continue mixing.

TABLE 4

Evaluation of the Foundation Cream Formulations

| Formulation | Comments |
|---|---|
| Control Foundation Cream | draggy, dry, not easy to spread |
| Control Foundation Cream + Emulsion I | easy to apply, smooth, non-tacky, soft after feel |
| Control Foundation Cream + Emulsion IV | easy to apply, spreadible, smooth, non-tacky, |
| Control Foundation Cream + Emulsion VIII | easy to apply, spreadible, smooth, soft after feel |
| Control Foundation Cream + Emulsion XI | dry, draggy, harsh |

Silicone latex emulsions I, IV and VIII improved ease of application and after feel of the foundation cream formulation, while the organic acrylate emulsion (XI) offered no improvement.

Example 4
Application of the Hydrophilic Silicone Latexes in Textile Treatments

Emulsions X and XI were diluted to 1% actives applied by dip and nip method onto polyester fabric (DACRON heatset Style 7774). Treated fabrics were dried in the textile oven at 100° C. for 3 minutes and evaluated for softness and wettability. Results are provided in Table 5. In this example the test procedures used were as follows:

Conditioning Textiles for Testing, ASTM Method D-1776-79

Absorbency of Bleached Textiles, AATCC Method 79-1992

Softness evaluation was done by the hand panel and the tested fabrics were ranked from the softest to the harshest (1 being the softest).

| Treatment | Softness Ranking*) | Wettability (sec) |
|---|---|---|
| Emulsion XI | 3 | 73 |
| Emulsion X | 1 | 55 |
| Water (control) | 2 | 180 |

*)lower rank means softer fabric

Silicone Latex Emulsion X imparted softness and hydrophilicity to the polyester fabric, while organic acrylate (XI) made the fabric hydrophilic but harsh.

We claim:
1. A liquid composition comprising:
a) a polymer formed from the polymerization in a solvent of monomers consisting essentially of acrylated or methacrylated polyether siloxane copolymers wherein the siloxane copolymer is of the formula

$$[R_3SiO_{1/2}]_m[O_{1/2}SiR_2O_{1/2}]_n[SiO_{3/2}R]_o[SiO_{4/2}]_p$$

wherein R is selected from $R^1$ and P, wherein each $R^1$ and P is the same or different and each $R^1$ is a monovalent hydrocarbon group; each P is $$R^3[O(C_bH_{2b}O)_zCOCR^4=CH_2]_g$$

wherein, $R^3$ is a polyvalent organic moiety, g is the valency of $R^3$ minus 1, $R^4$ is hydrogen or methyl; b=2 to 4, z=1 to 100, and m+n+p+o=1 to 100, at least one R is P; n=1 to 100; when o is not zero, n/o<10:1; when p is not zero, n/p<10:1; and m=0 to 10, with the proviso that the average acrylate functionality is >1 unsaturated groups (P) per molecule, and
b) said solvent.

2. A composition according to claim 1 wherein the copolymer is present at 1 to 50 weight percent of the composition.

3. A composition according to claim 2 wherein the solvent is water.

4. A composition according to claim 2 wherein the solvent is a cyclic or linear polydimethylsiloxane.

5. A composition according to claim 1 wherein the siloxane is of the formula $$QR^1{}_2Si[OSiR^1{}_2]_x[O-SiR^1P]_yOSiR^1{}_2Q$$

wherein each x and y are from 0 to 100; and Q is $R^1$ or P.

6. A composition comprising:
a polymer formed from the polymerization in a solvent of monomers consisting essentially of acrylated or methacrylated polyether siloxane copolymers wherein the siloxane copolymer is of the formula $$QR^1{}_2Si[OSiR^1{}_2]_xOSiR^1{}_2Q$$

wherein x is 0 to 100, each $R^1$ is an alkyl of 1 to 4 carbons, and each Q is $$R^3[O(C_bH_{2b}O)_zCOCR^4{=}CH_2]_g$$

wherein $R^3$ is a polyvalent organic moiety, g is the valency of $R^3$ minus 1, $R^4$ is hydrogen or methyl; b=2 to 4, z=1 to 100.

7. A composition according to claim 1 wherein the siloxane copolymer is acrylated.

8. A composition according to claim 1 wherein g=1.

9. A personal care formulation comprising the composition of claim 8.

10. A process comprising polymerizing monomers consisting essentially of an acrylate or methacrylate polyether siloxane copolymer in a solvent to form a liquid composition of a polymer of said siloxane copolymer and said solvent, wherein the siloxane copolymer is of the formula $$[R_3SiO_{1/2}]_m[O_{1/2}SiR_2O_{1/2}]_n[SiO_{3/2}R]_o[SiO_{4/2}]_p$$

wherein R is selected from $R^1$ and P, wherein each $R^1$ and P is the same or different and each $R^1$ is a monovalent hydrocarbon group; each P is $$R^3[O(C_bH_{2b}O)_zCOCR^4{=}CH_2]_g$$

wherein, $R^3$ is a polyvalent organic moiety, g is the valency of $R^3$ minus 1, $R^4$ is hydrogen or methyl; b=2 to 4, z=1 to 100, and m+n+p+o=1 to 100, at least one R is P; n=1 to 100; when o is not zero, n/o<10:1; when p is not zero, n/p<10:1; and m=0 to 10, with the proviso that the average acrylate functionality is >1 unsaturated groups per molecule.

11. A process according to claim 10 wherein at least one other acrylate or methacrylate is present during polymerization.

12. A process according to claim 10 wherein the other acrylate or methacrylate is selected from the group consisting of: methyl acrylate, ethyl acrylate, butyl acrylate, amyl acrylate, 2-ethylhexyl acrylate, cyclohexyl acrylate, vinyl acrylate, allyl acrylate, hydroxyethyl acrylate, perfluoroethyl acrylate, isobornyl acrylate, phenoxyethyl acrylate, tetraethylene glycol diacrylate, tripropylene glycol diacrylate, and trimethylolpropane triacrylate.

13. A process according to claim 10 wherein the solvent is water.

14. A process according to claim 12 wherein z=3 to 30 and b=2.

15. A process according to claim 12 wherein there is a blend of anionic and silicone surfactants present during polymerization.

16. A composition comprising:
a copolymer formed from the polymerization in a cyclic or linear polydimethylsiloxane of an acrylated or methacrylated polyether siloxane copolymer with an acrylate or methacrylate wherein the siloxane copolymer is present at 1 to 99 percent by weight of the resulting copolymer.

17. A composition according to claim 16 wherein the acrylate or methacrylate is selected from the group consisting of, methyl acrylate, ethyl acrylate, butyl acrylate, amyl acrylate, 2-ethylhexyl acrylate, cyclohexyl acrylate, vinyl acrylate, allyl acrylate, hydroxyethyl acrylate, perfluoroethyl acrylate, isobornyl acrylate, phenoxyethyl acrylate, tetraethylene glycol diacrylate, tripropylene glycol diacrylate, and trimethylolpropane triacrylate.

18. A composition according to claim 16 wherein the polyether siloxane copolymer is of the formula $$QR^1{}_2Si[OSiR^1{}_2]_x[O-SiR^1P]_yOSiR^1{}_2Q$$

wherein x, and y are 0 or an integer, Q is $R^1$ or P, wherein $R^1$ is an alkyl of 1 to 4 carbons, each P is $$R^3[O(C_bH_{2b}O)_zCOCR^4{=}CH_2]_g$$

wherein, $R^3$ is a polyvalent organic moiety, g is the valency of $R^3$, $R^4$ is hydrogen or methyl; b=2 to 4, z=1 to 100, and with the proviso that the average acrylate functionality is >1 unsaturated groups per molecule.

19. An acrylated or methacrylated polyether siloxane copolymer wherein the siloxane copolymer is of the formula $$[R_3SiO_{1/2}]_m[O_{1/2}SiR_2O_{1/2}]_n[SiO_{3/2}R]_o[SiO_{4/2}]_p$$

wherein R is selected from $R^1$ and P, wherein each $R^1$ and P is the same or different and each $R^1$ is a monovalent hydrocarbon group; each P is $$R^3[O(C_bH_{2b}O)_zCOCR^4{=}CH_2]_g$$

wherein, $R^3$ is a polyvalent organic moiety equal to g+1, g is 2 or 3, $R^4$ is hydrogen or methyl; b=2 to 4, z=1 to 100, and m+n+p+o=1 to 100, at least one R is P; n=1 to 100; when o is not zero, n/o<10:1; when p is not zero, n/p<10:1; and m=0 to 10.

20. A copolymer according to claim 19 wherein P is derived from alkoxylated trimethylol propane monoallyl ether, glycerol monoallyl ether, pentaerythritol allyl ether or trisopropanol amine allyl ether, which allyl has been hydrosilated onto a siloxane backbone.

* * * * *